United States Patent [19]

Helbig et al.

[11] 4,041,154

[45] Aug. 9, 1977

[54] MAGNESIUM-CONTAINING PHARMACEUTICAL COMPOSITIONS

[75] Inventors: Joachim Helbig; Franz Fischer, both of Tutzing, Germany

[73] Assignee: Verla-Pharm Arzneimittel-Fabrik Apotheker H. J. v. Ehrlich, Tutzing, Germany

[21] Appl. No.: 658,717

[22] Filed: Feb. 17, 1976

[30] Foreign Application Priority Data

Feb. 20, 1975 Germany .............................. 2507354

[51] Int. Cl.$^2$ ................... A61K 31/195; A61K 33/14; A61K 33/18; C07C 101/22
[52] U.S. Cl. ................... 424/150; 260/534 E; 424/153; 424/319
[58] Field of Search ............... 424/319, 152, 153, 150; 260/534 E

[56] References Cited

U.S. PATENT DOCUMENTS

| | | | |
|---|---|---|---|
| 3,658,995 | 4/1972 | Marchetti | 424/319 |
| 3,674,882 | 7/1972 | Houlihan | 424/317 |
| 3,778,505 | 12/1973 | Saint Martin | 424/317 |
| 3,836,668 | 9/1974 | Batlles et al. | 424/319 |

*Primary Examiner*—Stanley J. Friedman
*Attorney, Agent, or Firm*—Browdy and Neimark

[57] ABSTRACT

The invention concerns magnesium-containing pharmaceutical compositions comprising at least one of magnesium diglutamate and magnesium diaspartate and one or more alkali or alkaline earth metal halogenide such as magnesium chloride, bromide or iodide, sodium or potassium chloride, bromide or iodide and calcium chloride, bromide or iodide. Combinations comprising lithium chloride or bromide and strontium chloride or bromide are also disclosed. The combinations are intended for use in raising magnesium levels in plasma and bone structures in warm blooded mammals.

3 Claims, No Drawings

MAGNESIUM-CONTAINING PHARMACEUTICAL COMPOSITIONS

This invention relates to a magnesium-containing pharmaceutical composition. More particularly, the invention relates to a magnesium-containing pharmaceutical composition comprising at least one of magnesium diglutamate and magnesium diaspartate.

Various magnesium-containing pharmaceutical compositions are known to be useful sedative/tranquilizers, muscle relaxants, and infarct prophylactics. Thus, for example, the complex magnesium glutamate hydrobromide is a known sedative and muscle relaxant, the complex magnesium aspartate hydrobromide is a known sedative/tranquilizer, and the complex magnesium aspartate hydrochloride is a known infarct prophylactic. The known complex magnesium glutamate hydrochloride behaves similarly and is useful for the same purpose as the complex magnesium aspartate hydrochloride. Also known are the complexes magnesium glutamate hydroiodide and magnesium aspartate hydroiodide which are particularly useful in magnesium therapy where thyroid gland disorders are present. These known complexes comprise 1 : 1 : 1 ratio of aminodicarboxylic acid : magnesium : halogen and are difficult to obtain at low cost and in a solid form suitable for pharmaceutical use other than by way of a special technique involving spray drying. Conventional techniques in general lead to hygroscopic and difficult to handle hard glass-like masses.

Complexes such as mentioned above are on the other hand superior to other magnesium-containing compounds useful for similar treatment in that they are for example better resorbed and also lead to improved magnesium uptake in bone structures as indicated by standard pharmacological test procedures on test animals.

It has been surprisingly found, in accordance with the invention, that simple mixtures or concomitant administration of one of magnesium diglutamate and magnesium diaspartate, together with at least one appropriate alkali or alkaline earth metal halogenide leads to the same improved properties as do the difficultly prepared complexes mentioned above. Thus, for example, concomitant administration or administration of a mixture of magnesium diaspartate and magnesium chloride, magnesium diaspartate and sodium or potassium chloride, or magnesium diaspartate and calcium chloride, most preferably in substantially equimolecular amounts, leads to pharmacological and therapeutic effects which are substantially the same as a corresponding dose (calculated on magnesium content) of the magnesium aspartate hydrochloride 1 : 1 : 1 complex described above. Similarly, for example, concomitant administration or administration of a mixture of magnesium diaspartate and magnesium bromide, magnesium diaspartate and sodium or potassium bromide, or magnesium diaspartate and calcium bromide, most preferably in substantially equimolecular amounts, leads to pharmacological and therapeutic effects which are substantially the same as a corresponding dose (calculated on magnesium content) of the magnesium aspartate hydrobromide 1 : 1 : 1 complex described above. Furthermore, for example, concomitant administration or administration of a mixture of magnesium diglutamate and magnesium chloride, magnesium diglutamate and sodium or potasium chloride, or magnesium diglutamate and calcium chloride, most preferably in substantially equimolecular amounts, leads to pharmacological and therapeutic effects which are substantially the same as a corresponding dose (calculated on magnesium content) of the magnesium glutamate hydrochloride 1 : 1 : 1 complex described above. The same holds true for concomitant administration or administration of a mixture of magnesium diglutamate and magnesium bromide, magnesium diglutamate and sodium or potassium bromide, or magnesium diglutamate and calcium bromide, most preferably in substantially equimolecular amounts, and the mixtures lead to pharmacological and therapeutic effects which are substantially the same as the magnesium glutamate hydrobromide 1 : 1 : 1 complex described above. Also, concomitant administration or administration of a mixture of one of magnesium diglutamate or magnesium diaspartate with magnesium iodide, sodium or potassium iodide or calcium iodide lead to pharmacological and therapeutic effects which are substantially the same as the magnesium hydroiodide and magnesium aspartate hydroiodide 1 : 1 : 1 complexes described above.

It will be understood from above that pharmaceutical preparations comprising magnesium diglutamate or magnesium diaspartate and an alkali or alkaline earth metal chloride are infarct prophylactics. Similarly, pharmaceutical preparations comprising magnesium diglutamate and an alkali metal or alkaline earth metal bromide are sedatives and muscle relaxants, and pharmaceutical preparations comprising magnesium diaspartate and an alkali metal or alkaline earth metal bromide are sedative/tranquilizers. Pharmaceutical preparations comprising magnesium diaspartate and an alkali metal or alkaline earth metal bromide are sedative/tranquilizers. Pharmaceutical preparations comprising magnesium diglutamate or magnesium diaspartate and an alkali metal or alkaline earth metal iodide are useful in magnesium therapy where thyroid gland disorders are present.

Where the alkali or alkaline earth metal halogenide chosen for the mixture is a sodium or potassium salt, the resulting mixture also finds application in the treatment of electrolyte imbalances.

Another aspect of the invention is concerned with concomitant administration or providing a mixture of one of magnesium diglutamate or magnesium diaspartate with a lithium halogenide, including particularly lithium chloride or lithium bromide. These mixtures exhibit anti-depressant activity in standard pharmacological tests in test animals.

A strontium halogenide, including particularly strontium chloride, may be employed as alkaline earth metal halogenide. Mixtures comprising a strontium salt are particularly useful in magnesium therapy of patients undergoing radioactive strontium treatment. Thus, $Sr^{90}$ levels in bone structure can be lowered.

Pharmaceutical preparations of the invention suitable for oral administration may be in the form of multi-layer tablets, one layer comprising one of the magnesium aminodicarboxyllic acids and another comprising the alkali or alkaline earth metal halogenide. Alternatively, the magnesium aminodicarboxylic acid and the alkali or alkaline earth metal halogenide may be provided separately or together as a loose-grained mixture in a capsule or as a granulate for mixing with water and drinking. Further, solutions of the active agents may be prepared.

Administration is preferably oral, but injectable solutions for parenteral administration, such as intramuscularly, may be provided.

Particularly advantageous resorption values have been noted when the preparations of the invention comprise a hydrophylic additive, preferably a carbohydrate easily soluble in water, mucoids, protein, alcohols, polyalcohols, polyvinylpyrrolidone, or silica gel, preferably in submicroscopic form, such as that available under the trademark Aerosil. Other conventional physiologically inert additives may be included.

The doses of the preparations of the invention which are administered will of course vary dependent on the compounds employed, the mode of administration and and the condition being treated. However, for each of the above-mentioned uses, and for each of the concomitant administrations or administration of the mixtures described, the daily doses of magnesium aminodicarboxylic acid (i.e. magnesium diglutamate or magnesium diaspartate) may be from about 0.2 to about 40 mg/kg animal body weight, and from about 0.15 to about 20 mg/kg animal body weight for the alkali or alkaline earth metal halogenide (preferably magnesium, potassium or calcium chloride or bromide). The daily oral dose for the larger mammals, of a weight of about 70 kg, is from about 80 to about 500 mg of aminodicarboxylic acid and from about 50 to about 2500 mg of alkali or alkaline earth metal halogenide, conveniently administered in divided doses two to four times a day. Unit oral dosage forms may comprise from about 10 to about 2500 mg of the magnesium aminodicarboxylic acid and from about 1.5 to about 1100 mg of the alkali or alkaline earth metal halogenide. Parenteral daily doses are from about 350 to about 2000 mg of the magnesium aminodicarboxylic acid and from about 140 to about 1000 mg of the alkali or alkaline earth metal halogenide, preferably administered once a day.

A series of daily and unit dose examples for magnesium diaspartate and various alkali or alkaline earth metal halogenides are listed below, and it will be appreciated that similar examples can be prepared for magnesium diglutamate and the various alkali or alkaline earth metal halogenides.

1. Preparations comprising magnesium diaspartate and magnesium chloride
   Unit dose, oral:
   between 225 mg magnesium diaspartate + 74 mg magnesium chloride
   and 2256 mg magnesium diaspartate + 744 mg magnesium chloride.
   Daily dose, oral:
   between 276 mg magnesium diaspartate + 124 mg magnesium chloride
   and 4962 mg magnesium diaspartate + 1638 mg magnesium chloride.
   Unit dose, parenteral:
   between 451 mg magnesium diaspartate + 149 mg magnesium chloride
   and 940 mg magnesium diaspartate + 310 mg magnesium chloride.
   Daily dose, parenteral:
   between 451 mg magnesium diaspartate + 149 mg magnesium chloride
   and 1880 mg magnesium diaspartate + 620 mg magnesium chloride.

2. Preparations comprising magnesium diaspartate and magnesium bromide
   Unit dose, oral:
   between 91 mg magnesium diaspartate + 58 mg magnesium bromide
   and 549 mg magnesium diaspartate + 351 mg magnesium bromide.
   Daily dose, oral:
   between 91 mg magnesium diaspartate + 58 mg magnesium bromide
   and 1465 mg magnesium diaspartate + 935 mg magnesium bromide.

3. Preparations comprising magnesium diaspartate and potassium chloride
   Unit dose, oral:
   between 198 mg magnesium diaspartate + 102 mg potassium chloride.
   and 1978 mg magnesium diaspartate + 1022 mg potassium chloride.
   Daily dose, oral:
   between 330 mg magnesium diaspartate + 170 mg potassium chloride.
   and 4351 mg magnesium diaspartate + 2249 mg potassium chloride.
   Unit dose, parenteral:
   between 395 mg magnesium diaspartate + 204 mg potassium chloride.
   and 824 mg magnesium diaspartate + 425 mg potassium chloride.
   Daily dose, parenteral:
   between 395 mg magnesium diaspartate + 204 mg potassium chloride.
   and 1648 mg magnesium diaspartate + 851 mg potassium chloride.

4. Preparations comprising magnesium diaspartate and potassium bromide
   Unit dose, oral:
   between 82 mg magnesium diaspartate + 68 mg potassium bromide.
   and 493 mg magnesium diaspartate + 407 mg potassium bromide.
   Daily dose, oral:
   between 82 mg magnesium diaspartate + 68 mg potassium bromide.
   and 1315 mg magnesium diaspartate + 1084 mg potassium bromide.

5. Preparations comprising magnesium diaspartate and calcium chloride
   Unit dose, oral:
   between 217 mg magnesium diaspartate + 83 mg calcium chloride
   and 2166 mg magnesium diaspartate + 833 mg calcium chloride.
   Daily dose, oral:
   between 361 mg magnesium diaspartate + 139 mg calcium chloride
   and 4766 mg magnesium diaspartate + 1834 mg calcium chloride.
   Unit dose, parenteral:
   between 433 mg magnesium diaspartate + 167 mg calcium chloride
   and 903 mg magnesium diaspartate + 347 mg calcium chloride.
   Daily dose, parenteral:
   between 433 mg magnesium diaspartate + 167 mg calcium chloride
   and 1805 mg magnesium diaspartate + 694 mg calcium chloride.

6. Preparations comprising magnesium diaspartate and calcium bromide
   Unit dose, oral:

between 89 mg magnesium diaspartate + 61 mg calcium bromide
and 532 mg magnesium diaspartate + 368 mg calcium bromide.

Daily dose, oral:
between 89 mg magnesium diaspartate + 61 mg calcium bromide
and 1418 mg magnesium diaspartate + 982 mg calcium bromide.

What is claimed is:

1. A pharmaceutical preparation useful as an infarct prophylactic, a sedative and muscle relaxant, or a sedative and tranquilizer, comprising in combined form one of magnesium diglutamate and magnesium diaspartate, and at least one alkali or alkaline earth metal halogenide selected from magnesium chloride, magnesium bromide, magnesium iodide, sodium or potassium chloride, sodium or potassium bromide, sodium or potassium iodide, calcium chloride, calcium bromide, and calcium iodide, the ratio of the alkali or alkaline earth metal halogenide to the one of magnesium diglutamate and magnesium diaspartate being substantially equimolecular.

2. A pharmaceutical preparation useful as an infarct prophylactic, a sedative and muscle relaxant, or a sedative and tranquilizer, comprising in combined form one of magnesium diglutamate and magnesium diaspartate, and at least one alkali or alkaline earth metal halogenide selected from lithium chloride, lithium bromide, and strontium chloride, the ratio of the alkali or alkaline earth metal halogenide to the one of magnesium diglutamate and magnesium diaspartate being substantially equimolecular.

3. A pharmaceutical preparation according to claim 1, in which the components of the combination are associated with a hydrophylic substance selected from a hydrophylic water soluble carbohydrate, mucoid, protein, alcohol, polyalcohol, polyvinylpyrrolidone and silica gel.

* * * * *